(12) United States Patent
Faccioli et al.

(10) Patent No.: US 6,461,358 B1
(45) Date of Patent: Oct. 8, 2002

(54) DEVICE FOR THE EXTERNAL FIXATION OF BONES FRACTURES, IN PARTICULAR ANKLE FRACTURES

(75) Inventors: Giovanni Faccioli, Monzambano; Daniele Venturini, Povegliano Veronese, both of (IT)

(73) Assignee: Orthofix, S.r.l., Milan (IT)

( * ) Notice: Subject to any disclaimer, the term of this patent is extended or adjusted under 35 U.S.C. 154(b) by 0 days.

(21) Appl. No.: 09/869,402

(22) PCT Filed: Dec. 13, 1999

(86) PCT No.: PCT/EP99/09846

§ 371 (c)(1),
(2), (4) Date: Jun. 27, 2001

(87) PCT Pub. No.: WO00/40163

PCT Pub. Date: Jul. 13, 2000

(30) Foreign Application Priority Data

Dec. 31, 1998 (EP) .............................................. 98830807

(51) Int. Cl.⁷ ............................................... A61B 17/66
(52) U.S. Cl. ....................................................... 606/57
(58) Field of Search ............................. 606/53, 54, 56, 606/57, 58, 59, 105

(56) References Cited

U.S. PATENT DOCUMENTS

| | | | | |
|---|---|---|---|---|
| 2,393,831 A | * | 1/1946 | Stader | 606/57 |
| 4,696,293 A | * | 9/1987 | Ciullo | 128/98 ZK |
| 5,405,347 A | * | 4/1995 | Lee et al. | 606/54 |
| 5,662,650 A | | 9/1997 | Bailey et al. | |
| 5,827,282 A | * | 10/1998 | Pennig | 606/54 |
| 6,024,745 A | * | 2/2000 | Faccioli et al. | 606/54 |

FOREIGN PATENT DOCUMENTS

| | | |
|---|---|---|
| DE | 2745504 A | 4/1979 |
| EP | 611 007 A1 | 8/1994 |
| WO | WO 96/12443 A | 5/1996 |
| WO | WO 97/10775 A | 3/1997 |

* cited by examiner

*Primary Examiner*—Eduardo C. Robert
(74) *Attorney, Agent, or Firm*—Leydig, Voit & Mayer, Ltd.

(57) ABSTRACT

The invention relates to an improved device for external fixation of bone fractures, specifically for ankle fractures, of the type adapted for mounting to a unilateral external fixator and comprising an extendible central body and opposed articulated portions which are connected to the respective ends of the central body by ball joints. The device is an ankle clamp having a stem, preferably made of a transparent material to X-radiation, with a bifurcated end formed with a pair of prongs having a first jaw portion of a tilting clamp journalled on a pivot provided between the prongs and comprises a second jaw portion coupled to the first jaw portion and fastened thereto by a pair of screws.

19 Claims, 11 Drawing Sheets

FIG. 3
FIG. 4
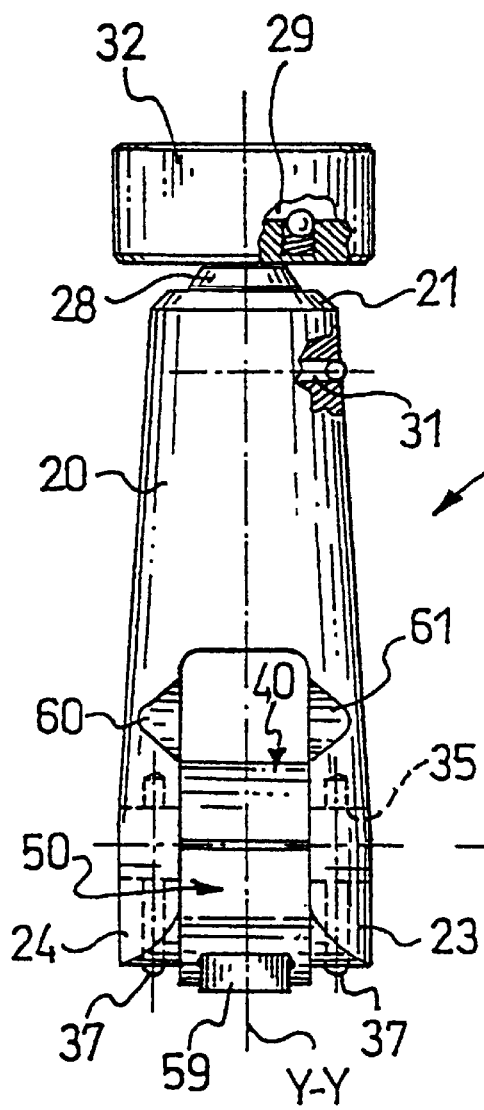
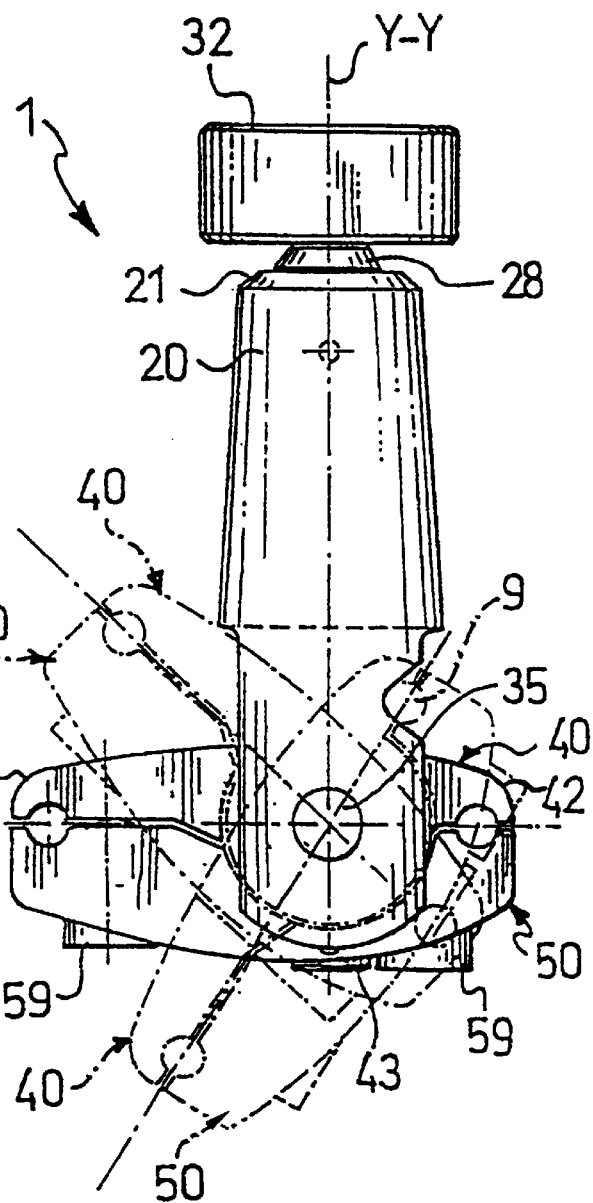

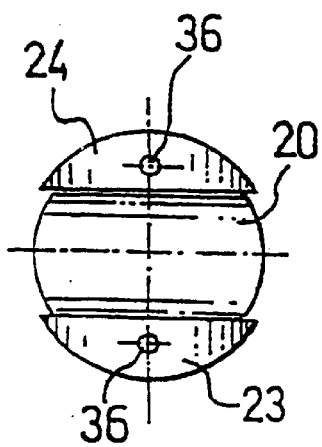
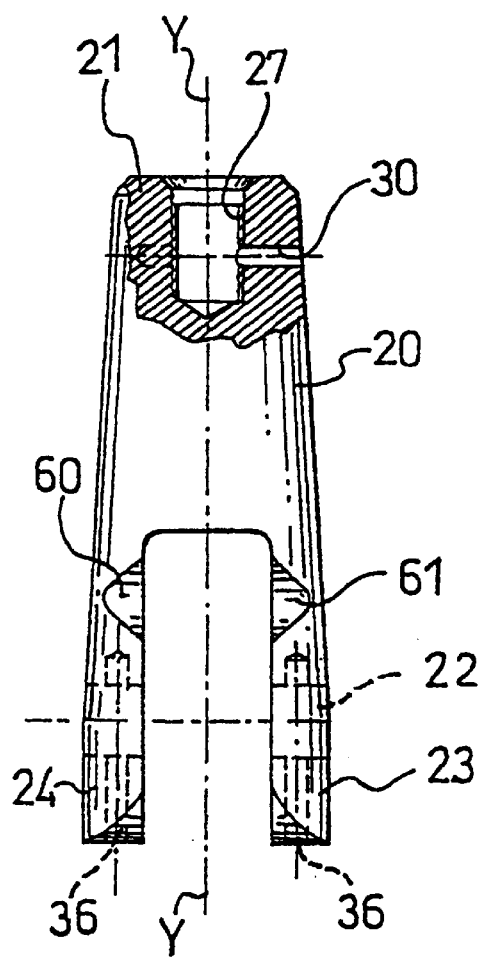
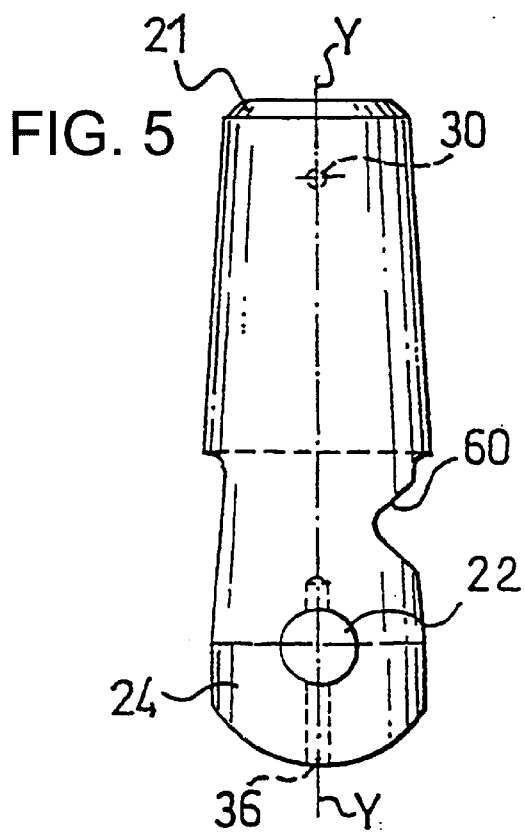

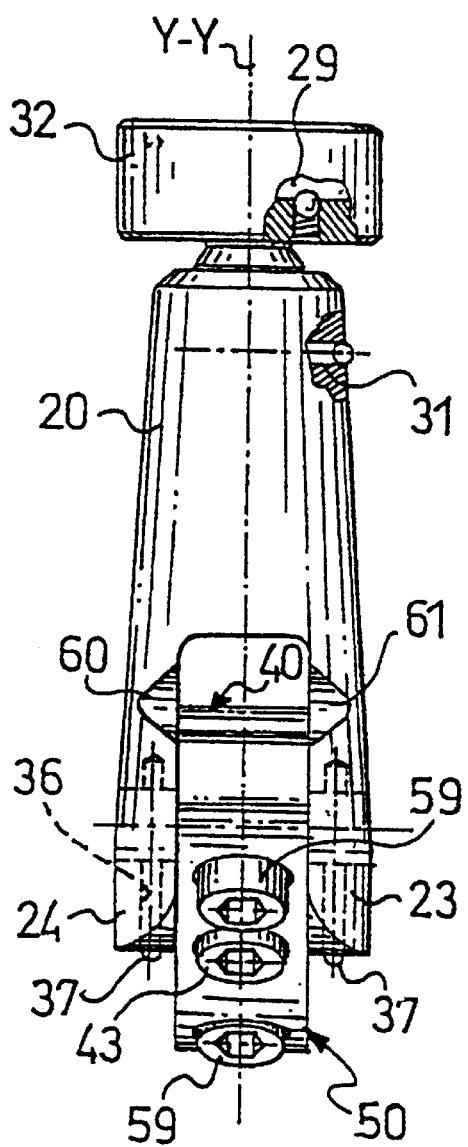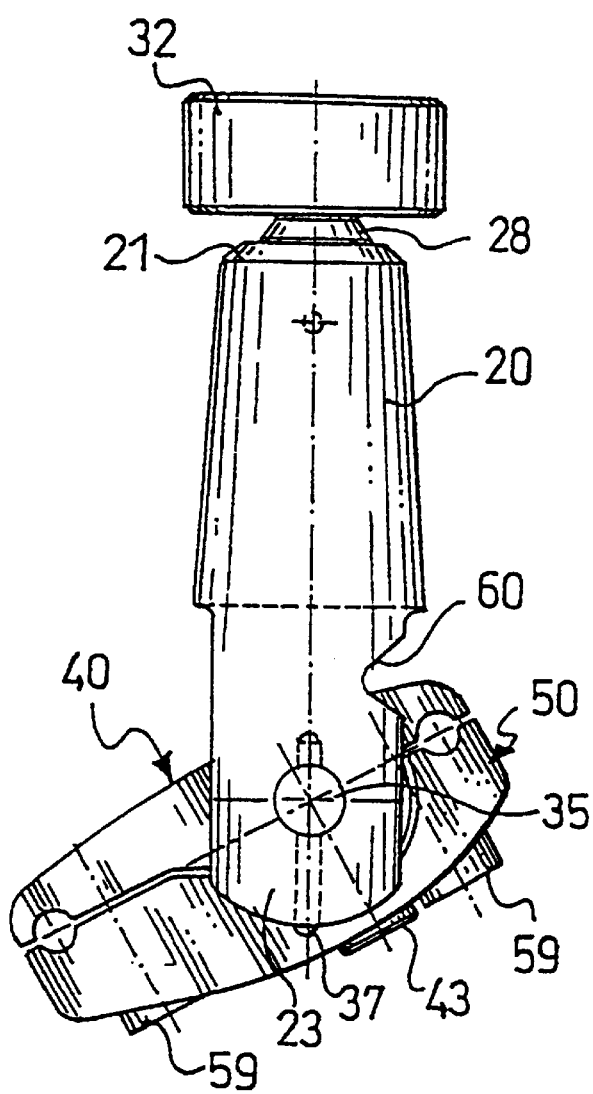

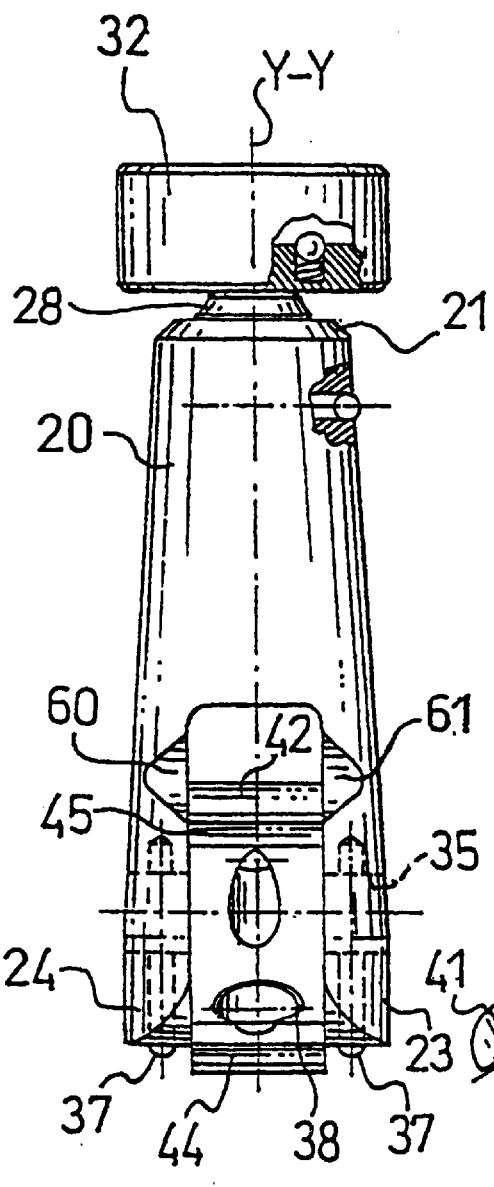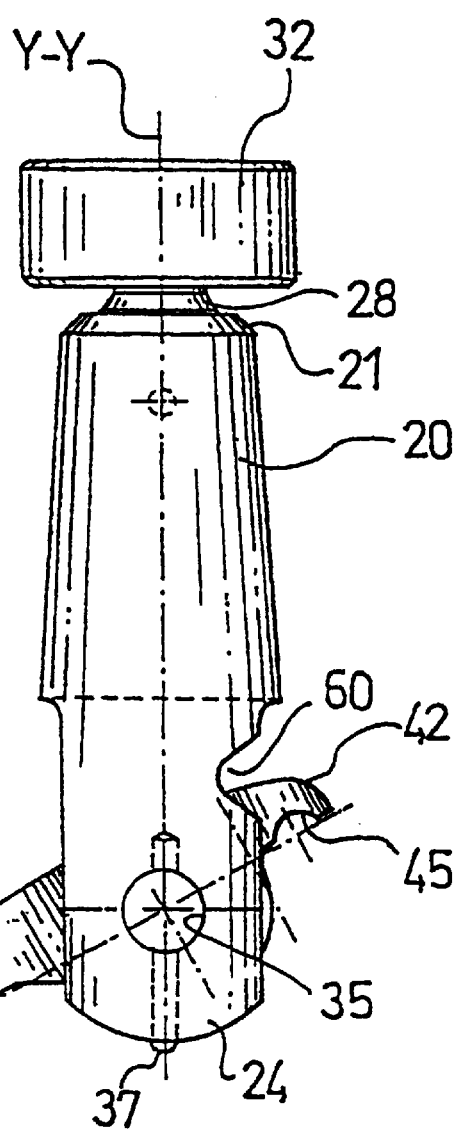

DEVICE FOR THE EXTERNAL FIXATION OF BONES FRACTURES, IN PARTICULAR ANKLE FRACTURES

FIELD OF THE INVENTION

This invention relates to an improved device for the external fixation of bone fractures, in particular ankle fractures.

More specifically, the invention relates to a device adapted for mounting to an external fixator and comprising an extendible central body and opposed articulated portions which are connected to respective ends of the central body by ball joints.

PRIOR ART

The use of external fixators capable of setting bone fractures in highly delicate regions of the human skeleton, and especially in the proximity of joints, is common practice in the instant field.

As an example, for treating fractures of the tibial stem, and to prevent the inception of arthrodesy and arthrodiastasis of the ankle, unilateral external fixators are often used which have a main body and articulated portions joined to the central body by means of ball joints. The articulated portions are to be secured to the tibia and the ankle bones by means of rod-like fastening screws.

A prior external fixator for setting fractured ankles is described, for example, in the International Patent Application No. WO97/10775 to this same Applicant.

Also as an example, FIG. 1 of the accompanying drawings illustrates the use of a fixator sold by the Applicant. To more clearly show how this fixator is applied, the perspective view of FIG. 1 includes the bone parts affected by the operation, namely a tibia T and tibia-tarsus joint Ts.

The fixator shown in FIG. 1 comprises a central body 2 of substantially cylindrical shape that can be extended axially and has opposite ends attached to respective articulated portions 3 and 4.

A first portion 3, referred to as proximal hereinafter, is secured realisably to the tibia by means of rod-like screws 5, which are threaded into the shinbone. Two or three of such screws usually provide sufficient holding power.

The proximal portion 3 is connected to one end of the central body 2 through a ball joint 6 which has Allen screw fasteners associated therewith at that end of the central body 2.

A second articulated portion 4, referred to as distal portion, is secured realisably to the ankle bones by means of rod-like screws 9 which are threaded into the talus and the calcaneus, respectively. The distal portion 4 is connected to the other end of the central body 2 through a ball joint 6, also having Allen screw fasteners associated therewith.

The distal portion 4 is better known in the art as the "ankle clamp", and will be indicated by this term hereinafter.

The ankle clamp 4 in FIG. 1 comprises a bifurcate stem 10 having a pair of prongs 11, 12 whose free ends mount a clamp member 15. The prongs 11, 12 are bored through across each free end. The through-going bores at the two ends are coaxial and accommodate an Allen-head bolt.

The clamp member 15 comprises a pair of jaws 16, 17 having mating inward contours which fit centrally around the bolt shank and clamp with their ends around the rod-like screws 9 to immobilise the calcaneus and tarsus. Coaxial holes are provided through the opposite ends of the jaws 16, 17 to receive respective bolts 18, 19 for tightening the jaws onto the rod-like screws 9.

While being advantageous in many ways and substantially serving its purpose, the above ankle clamp has some drawbacks, as follows.

Since the clamp member 15 with the jaws 16, 17 is fastened to the prongs 11,12 of the bifurcate stem 10 by means of an Allen-head bolt, is difficult for the surgeon to couple the components of the clamp. Moreover, two different clamp members must be used depending to the use on a right or a left limb respectively.

Moreover, the clamp stem partly conceals the joint, so that the surgeon is forbidden a clear view of the tibia-tarsus joint, even if radiographic.

This represents a serious shortcoming because a restricted view of the joint makes more difficult reducing the fracture, and also inspecting the healing bone periodically for later evaluation; most importantly, a restricted view of the joint makes very difficult the locating of the pivot centre of the tibia-tarsus joint, on which depends the proper positioning of the screws in the calcaneus and the talus for securing the clamp.

If the pivot centre as estimated by the surgeon does not correspond with the true pivot centre of the ankle, the joint may undergo diastasis and compression, and ligaments become strained.

To obviate, at least in part, these drawbacks, a solution has been proposed in the art and described in sales catalogues. This prior solution consists of providing the ankle clamp with a C-shaped stem effective to leave the surgical area view unobstructed.

However, this prior solution is unsatisfactory on account of the following:

The C-shaped stem is not coaxial with the other portions of the fixator, which potentially detracts from the overall structure rigidity;

A fixator having a C-shaped stem cannot be used for left-side and right-side broken limbs; thus, separate fixators must be made available for application to left and right limbs, since converting an fixator on the occasion of a surgical intervention would be an inconvenient and complicated procedure;

The C-shaped stem produces an offset bulk which can be of hindrance to the surgeon during the operation, as well as to the convalescing patient;

Finally, there still exists a blocked direction to X-raying.

The underlying technical problem of this invention is that of providing an improved ankle clamp which can be easily and directly used for both left- and right-side broken limbs.

Another aim of the present invention is that of contriving an improved ankle clamp having such construction and functional features to provide the surgeon with an unrestricted view of the joint being treated from all directions, while holding the fixator coaxial with the ankle clamp mounted to it.

SUMMARY OF THE INVENTION

The above technical problem is solved by a device as previously indicated and defined in the characterising portions of Claim 1 and following.

The features and advantages of an ankle clamp according to the invention will be apparent from the following description of an embodiment thereof, given by way of non-limiting example with reference to the accompanying drawings.

BRIEF DESCRIPTION OF THE DRAWINGS

FIGS. 3 and 4 are an elevation and a part-sectional view, respectively, of the clamp of FIG. 2, as viewed from one side and head-on.

FIGS. 5 and 6 are an elevation and a part-sectional view, respectively, of a detail of the clamp of FIG. 2, as viewed head-on and from one side.

FIG. 7 is a view from below of the same detail as in FIG. 5.

FIGS. 8 and 9 are an elevation and a part-sectional view, respectively, of the clamp of FIG. 2, as viewed from one side and head-on at different angular settings of its parts.

FIGS. 16 and 17 are respective elevation views of the clamp of FIG. 2, as viewed head-on and from one side, with only the detail of FIG. 10 in place.

DETAILED DESCRIPTION

Figure 2:
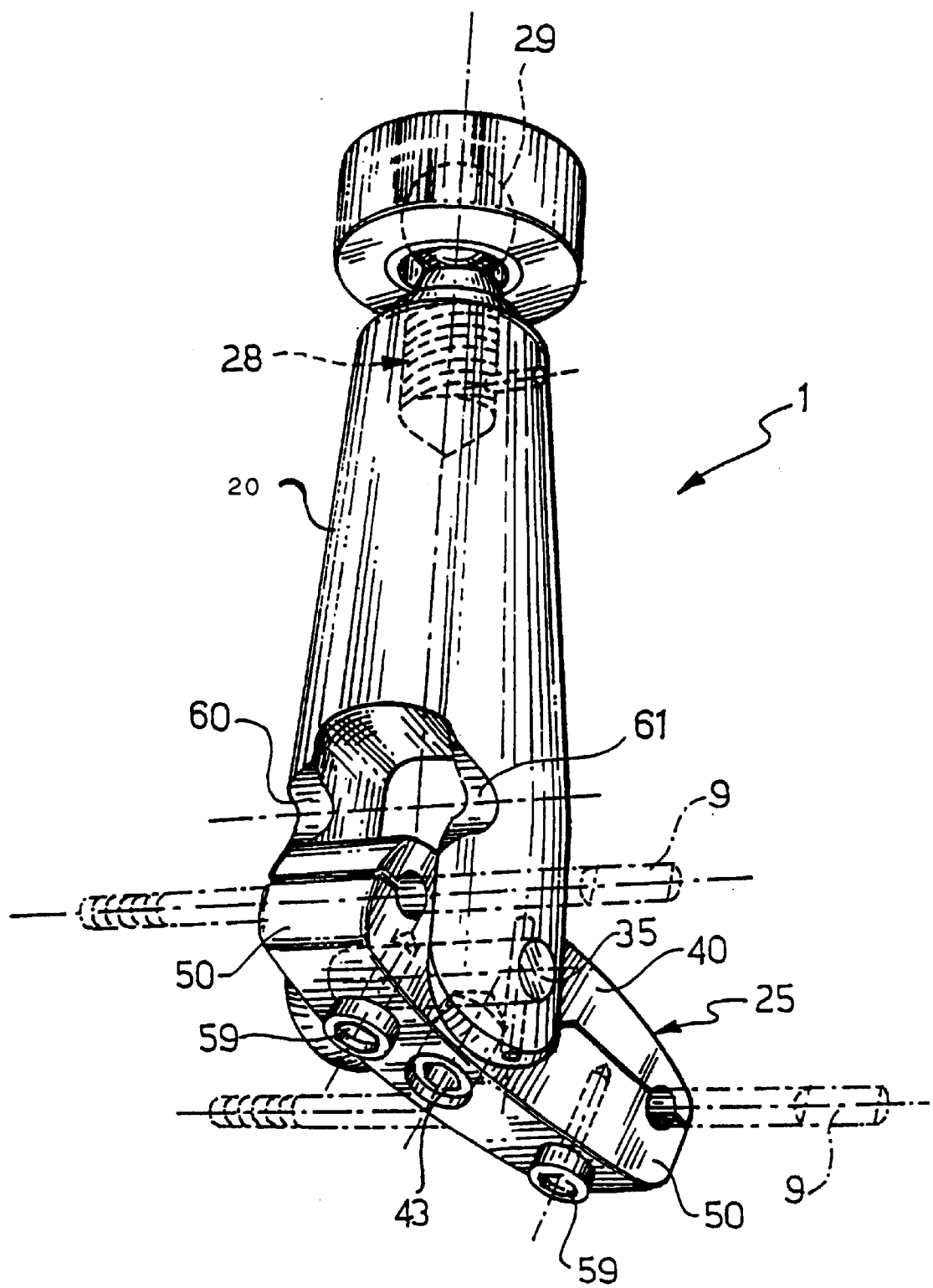
FIG. 2 is a perspective view of an ankle clamp according to this invention.
Figure 2A:
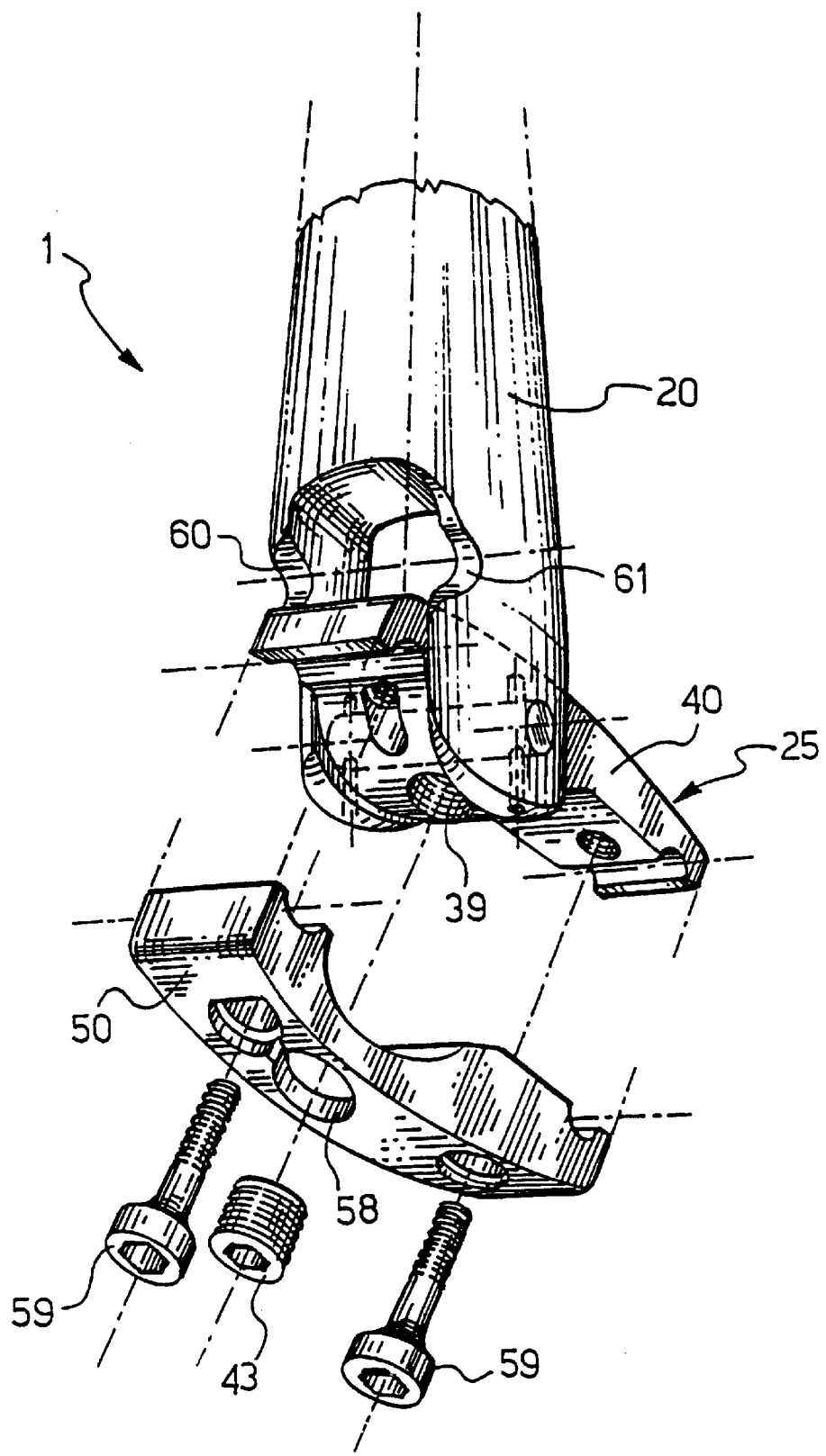
FIG. 2A is a partly exploded view showing the ankle clamp of FIG. 2 in perspective.
Figure 2B:
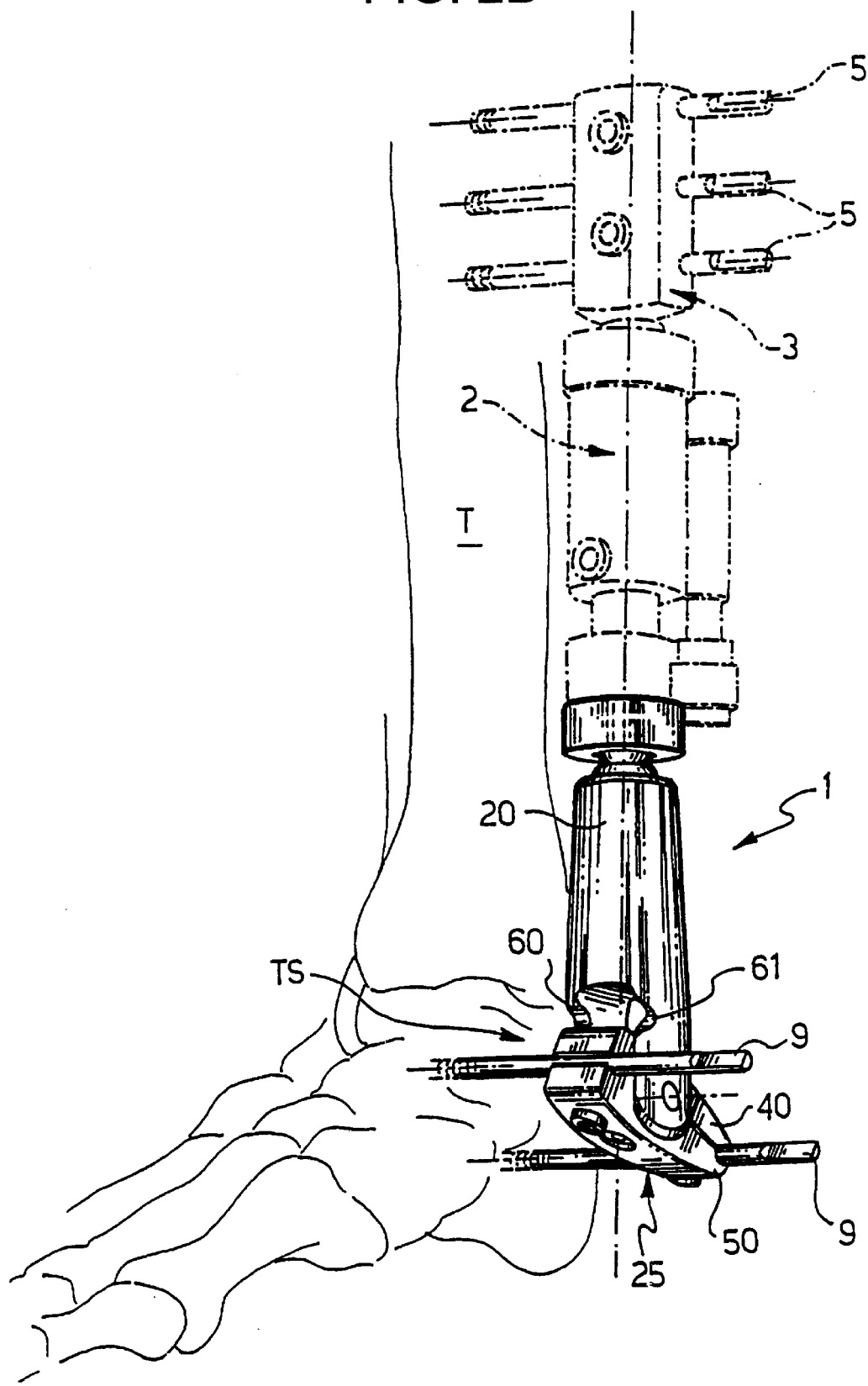
FIG. 2B is a further perspective view of the ankle clamp of FIG. 2 in use.
Figure 12:
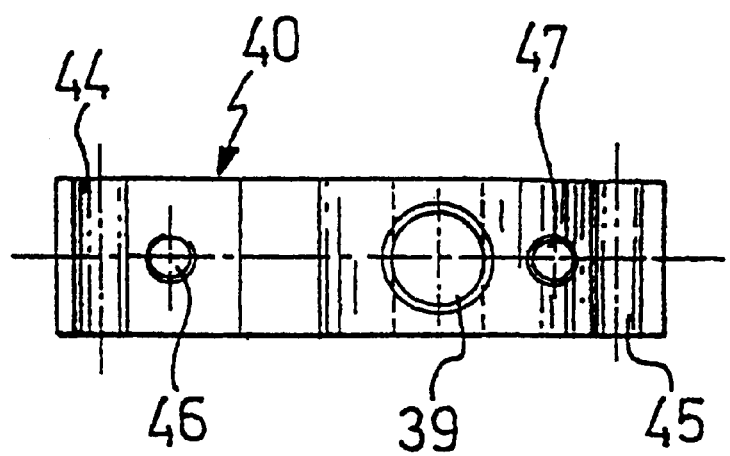
FIGS. 10, 11 and 12 are front, vertical cross-section, and bottom views, respectively, of a detail of the clamp of FIG. 2.

Referring in particular to the example of FIG. 2 of the drawings, generally and schematically shown at 1 is an improved device according to this invention, adapted for external fixation of fractures, specifically a broken tibia stem and broken ankle.

Figure 1:
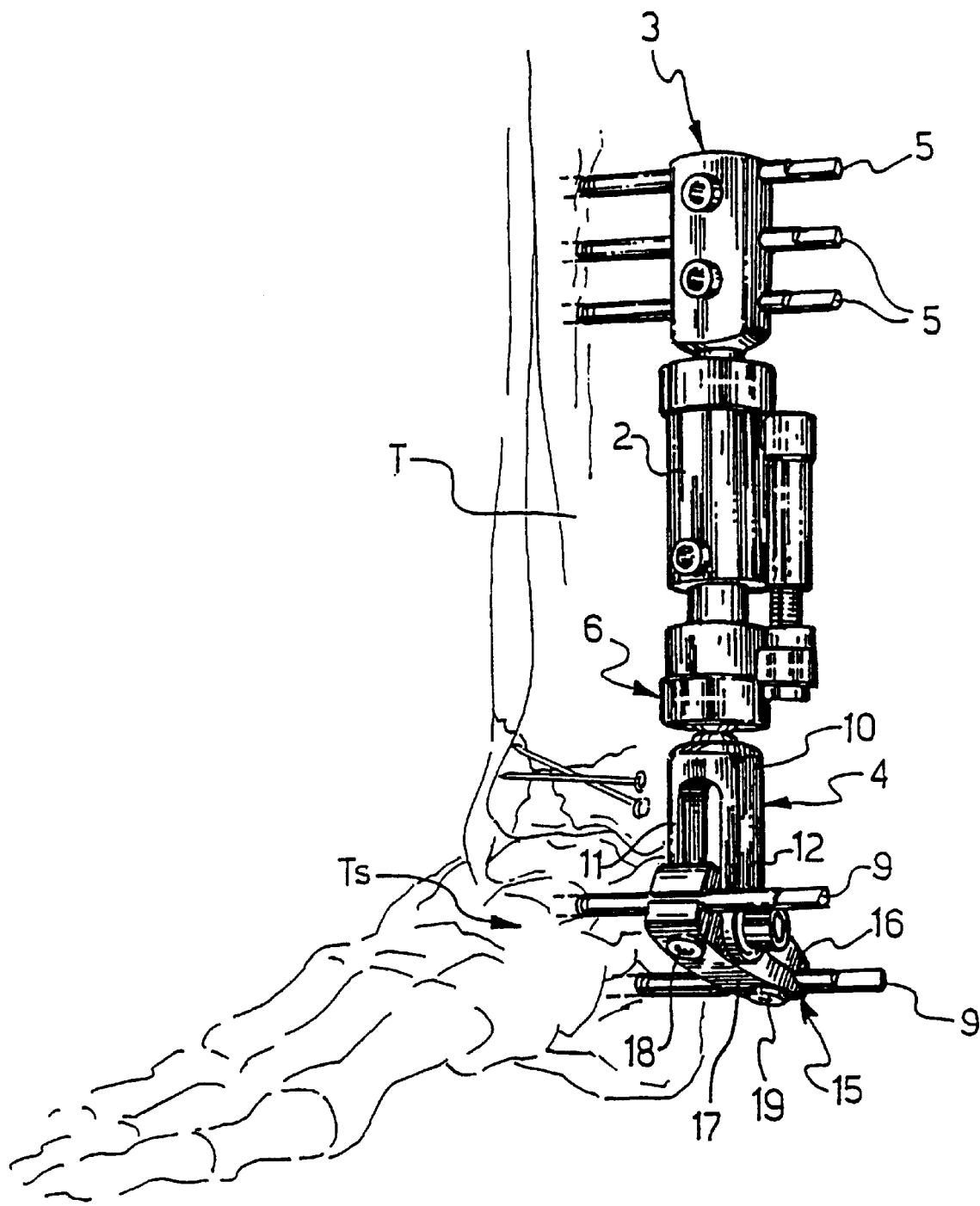
FIG. 1 is a perspective view showing schematically a state-of-art external fixator for reducing broken ankles.

The device 1 is intended for mounting to a unilateral external fixator for reducing fractures, e.g. the fixator previously discussed in relation to FIG. 1.

As said before, a fixator adapted to incorporate the device 1 would comprise a central body 2 and opposed portions articulated to respective ends of the central body. The device 1 of this invention forms one of these articulated portions, specifically the distal articulated portion defining an ankle clamp.

This ankle clamp comprises a main body formed as an elongate stem 20 of frusto-conical shape, and a tilting clamp 25 mounted pivotally to one end of the stem 20.

The stem 20 has one end 21 connected to the central body of the fixator, which end will be termed the upper end hereinafter. The other or lower end of the stem 20 is bifurcated and includes a pair of prongs 23, 24 having the tilting clamp 25 mounted therebetween.

In a known manner, a socket 27 is provided in the upper end 21 of the stem 20 for receiving a threaded stud 28 formed with a ball head 29. The socket extends coaxially with the axis Y of the stem 20, and is communicated laterally to a hole 30 drilled transverse to the axis Y, as shown in FIG. 6. The hole 30 accommodates a lockpin 31 to block the stud 28 in the end 21 of the stem 20.

The ball head 29 of the stud 28 is a part of a ball joint 6 connecting the clamp 1 to the central body of the fixator. The head 29 is received in a mating socket formed in one end of the central body, and is held in place by an internally grooved ring nut 32.

The lower end of the stem 20 will now be discussed in detail.

The free ends of the prongs 23, 24 are each provided with a through-going hole 22 whose axis lies transverse to the axis Y of the stem 20. The holes through the two ends are coaxial with each other and receive respective opposed ends of a cross-pivot 35 carrying the tilting clamp 25.

Advantageously in this invention, the stem 20 is made of a transparent material to X-ray.

More particularly, the preferred stem 20 is a fiber-reinforced plastics matrix.

In the embodiment under consideration by way of non-limitative example, a polyetherterketone or Peek matrix with a 30% carbon fibre filler is used. The carbon fibres have the purpose of making the clamp stem adequately rigid.

Of course, other matrices and filler proportions could be used instead.

For example, a carbon fibre fill of less than 30%, i.e. in the 20% to 30% range, could still provide sufficient rigidity, and enhance the transparency to X-radiation.

A fibre fill above 30%, i.e. in the 30% to 50% range, could impart sufficient rigidity without significantly deteriorating the characteristic transparency to X-radiation of the inventive stem. Furthermore, different techniques may be employed in the construction of this stem. As an example, the stem could be machined from bar stock, or injection moulded, or formed by an RTM process.

The other parts of the device 1, which need not be transparent to X-radiation, are preferably formed from an aluminium alloy and surface treated by heavy anodic oxidation.

It should be noted that the reinforcing filler confers so much strength on the stem 20 structure that additional holes can be drilled therethrough. In particular, the free end of each of the prongs 23, 24 can be drilled with a hole 36 along a parallel direction to the axis Y of the stem 20.

Each hole 36 crosses the bore 12 accommodating an end of the pivot 35. Each of the holes 36 is to receive a corresponding lockpin 37 for the respective end of the pivot 35.

Advantageously, the tilting clamp 25 includes a first jaw portion 40 journalled on the pivot 35 between the prongs 23 and 24 of the stem 20. This jaw 40 comprises a central portion having a rounded outline and wherethrough a central hole 38 is provided. Two opposed jutting portions 41. 42 are integral with said central portion.

FIG. 16 is a front view of an example of the ankle clamp according to the invention, wherein the lower end of the stem 20 mounts the first jaw 40 only.

Provided at each of the jutting portions 41, 42 ends are respective semicylindrical sockets 44, 45 for accommodating a section each of the rod-like screws fitted in the talus or the calcaneous, in co-operation with a mating socket formed in a second jaw portion 50 of the tilting clamp 25 and described hereinafter.

The axes of the two semicylindrical sockets 44, 45 lie parallel to and in the same plane P as the axis of the hole 38. Formed in the proximity of each of the ends of the jutting portions 41, 42 is a threaded socket 46, 47 extending through the jutting portions along a perpendicular direction to said plane P.

Figure 11:
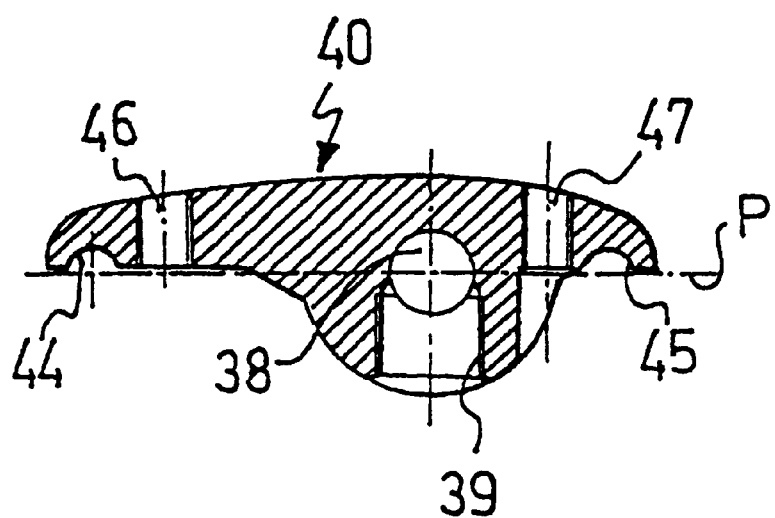
Figure 10:
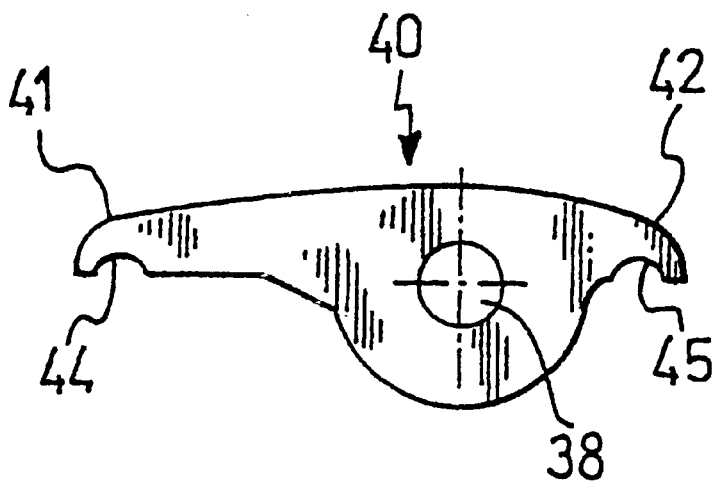
Figure 15:
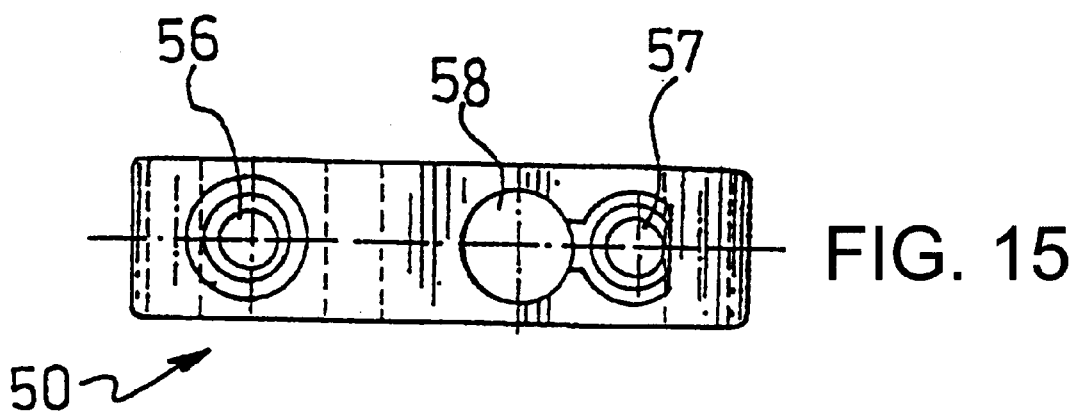
FIGS. 13, 14 and 15 are top, front, and bottom views, respectively, of a further detail of the clamp of FIG. 2.
Figure 14:
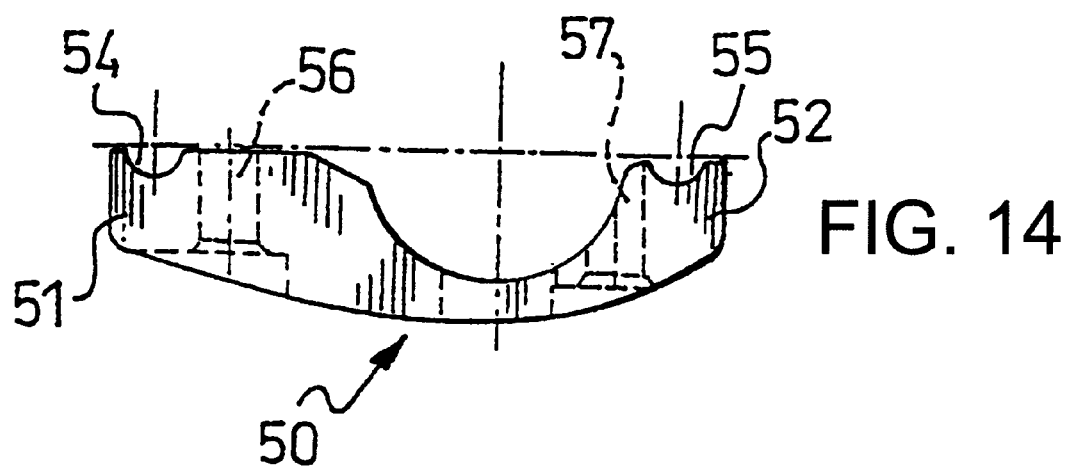
Figure 13:
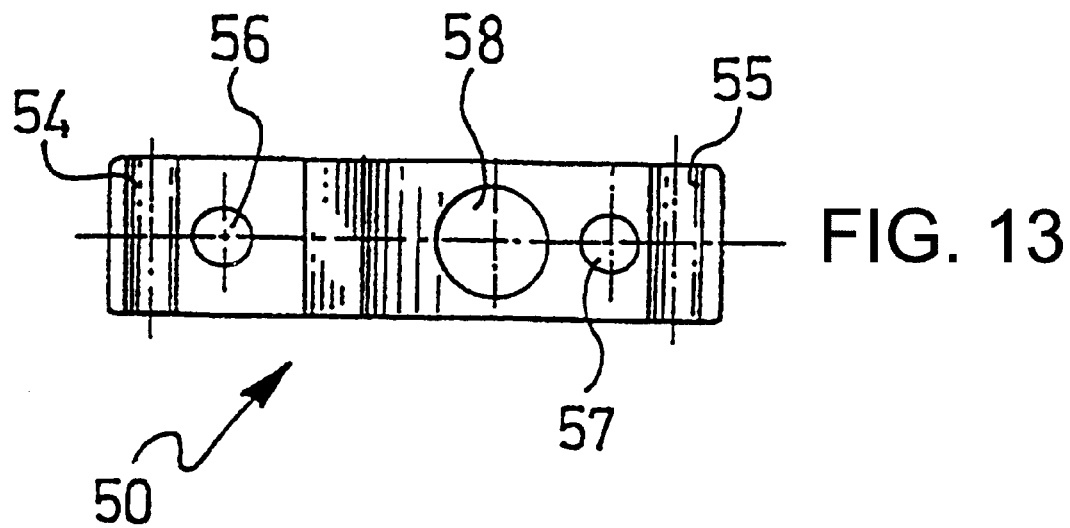
Figure 18:
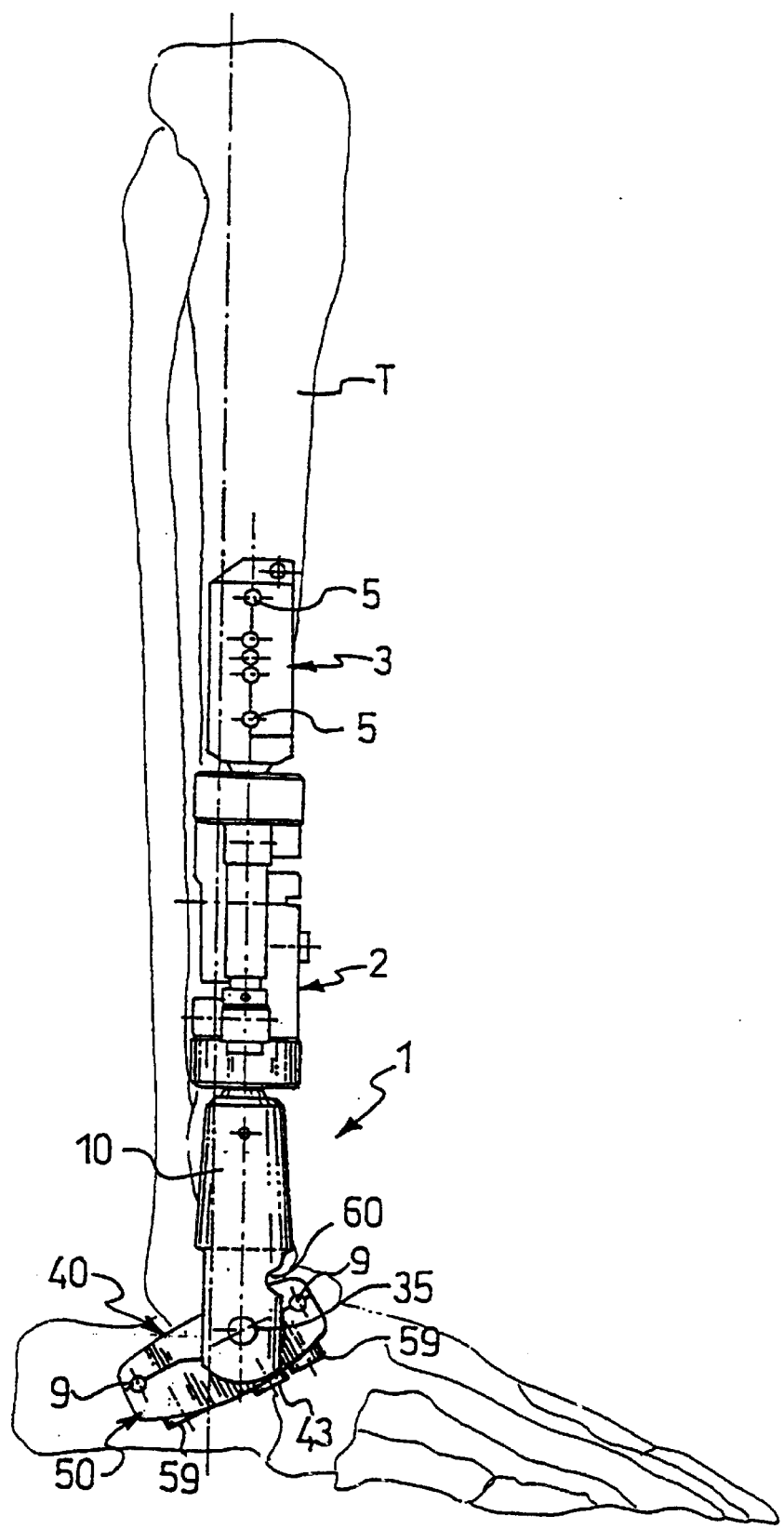
FIG. 18 is a schematic elevation view illustrating an application of the ankle clamp according to the invention to an external fixator.

Another threaded socket 39 is formed perpendicularly to the axis of the hole 38 in communication with the latter, as shown best in FIG. 11.

The threaded socket 39 is to receive an Allen-head screw fastener, e.g. a grub screw, for setting the portion 40 of the tilting clamp 25 to a preferred position, as decided by the surgeon, where said plane P would be inclined at a predetermined angle to the axis Y of the stem 20.

The tilting clamp 25 comprises a second jaw 50 whose internal contour matches that of the first jaw 40. This second jaw 50 also has jutting portions 51, 52, each provided with a respective semicylindrical socket 54, 55 in its end for cooperation with the matching sockets 44, 45 in holding a section of one of the rod-like screws 9 fitted in the talus or the calcaneous.

The jaws 40 and 50 are brought together with their internal contours in mating relationship, and secured by a pair of screw fasteners 59 passed through holes 56, 57 drilled in the second jaw 50 in alignment with the threaded sockets 46, 47 of the first jaw 40. Preferably, the screws 59 are Allen screws.

Furthermore, a hole 58 through the second jaw 50 allows the screw 43 to reach as far as the threaded socket 39 and engage it. In this way, the pivotal movement of the tilting clamp 25 can be stopped by tightening down the screw 43 in its threaded socket 39 such that it will interfere with the pivot 35 and produce a binding action.

Referencing to the axis Y of the stem 20, and assuming for the tilting clamp 25 an inclination angle of 0° with respect to the plane P lying perpendicularly to the axis Y, as shown in FIG. 4, an angular travel through a range of at least +44° to −58° is ensured for the portion 40.

This wide angular travel range, wider than any other prior solution, is also contributed by another feature of the ankle clamp according to this invention.

Lateral recesses 60 and 61 are provided, in fact, in the stem 20, on one side thereof, and in each of the prongs 23, 24 close to their attaching bases to the stem 20.

These recesses 60, 61 allow the angular travel range of the tilting clamp 25 to be extended, since one of the rod-like screws 9 used for securing to the talus or the calcaneous, being held in the jaws 40, 50 and extending transverse to the axis Y of the stem 20, can be accommodated within the recesses 60, 61 and made to abut against the prongs 23, 24.

Thus, the device of this invention does solve the technical problem, and achieves a number of advantages, foremost among which is that the X-ray transparency of the clamp stem affords the surgeon an unrestricted view of the joint affected by the fracture reduction operation from all perpendicular directions to the tibia axis.

In addition, the tilting portion of the clamp can be used in an universal and reversible fashion on a right-side limb or a left-side limb, this being accomplished without the clamp structure or the application technique having to be altered.

As can be appreciated, the tilting portion of the clamp may even be used on stem that don't present the feature of the X-ray transparency.

The clamp of this invention can be made of materials which allow of full preparatory sterilisation. In fact, this clamp can be sterilised by any of the most widely used processes, such as steam, ethylene oxide, or gamma radiation sterilisation.

The ankle clamp of this invention has an important advantage in that it can be retrofitted to existing fixators, thereby furnishing them with X-ray transparency in the area of the tibia-tarsus joint, as well as with universal applicability to either side limbs.

Changes and modifications can be made unto the device according to the invention within the scope of the following claims.

What is claimed is:

1. An ankle clamp device for external fixation of ankle bone fractures, said ankle clamp device being adapted for mounting to a distal end of a unilateral external fixator by means of at least one ball joint, the ankle clamp device comprising a stem with a bifurcate end formed with a pair of prongs, and a tilting clamp comprising a first jaw portion and a second jaw portion, the first jaw portion having a central portion and two opposed jutting portions formed integrally with the central portion, the tilting clamp being journalled between said prongs through said central portion.

2. A device according to claim 1, wherein the stem has an axis and the prongs each have a free end, each of the free ends of the prongs having a bore, said bores defining an axis, said bore axis being transverse to the axis of the stem, said device further comprising a transverse pivot carrying said first jaw portion and having opposed ends, the bores through the prong ends being coaxial with each other and receiving respective opposed ends of said transverse pivot carrying said first jaw portion of the tilting clamp.

3. A device according to claim 2, wherein said second jaw portion is coupled to the first jaw portion, and wherein the tilting clamp is journalled for pivotal movement, the second jaw portion comprising a hole and the first jaw portion comprising a threaded socket, the device further comprising a screw disposed through the hole and engaged in the threaded socket, the pivotal movement of the tilting clamp being stopped by said screw passed through the hole in the second jaw portion and engaged in the threaded socket provided in the first jaw portion, said screw interfering with said pivot.

4. A device according to claim 2, wherein said central portion includes a central portion bore formed centrally therethrough to accommodate said pivot, the central portion bore including a central portion bore axis, said first jaw portion further comprising a threaded socket formed perpendicularly to the central portion bore axis of the central portion bore and communicating therewith.

5. A device according to claim 2, wherein said stem is formed from a fibre-reinforced plastics matrix transparent to X radiation.

6. A device according to claim 1, further comprising a pair of screws and wherein said second jaw portion is coupled to the first jaw portion and fastened thereto by said pair of screws.

7. A device according to claim 6, wherein said second jaw portion and said first jaw portion have mating internal contours.

8. A device according to claim 6 wherein said stem is formed from a fibre-reinforced plastics matrix transparent to X radiation.

9. A device according to claim 1, wherein the stem has recesses formed laterally in each of the prongs.

10. A device according to claim 6, wherein said recesses are formed in a side of the prongs proximal a base of said bifurcate end.

11. A device according to claim 9 wherein said stem is formed from a fibre-reinforced plastics matrix transparent to X radiation.

12. A device according to claim 1, wherein said stem is made of a material transparent to X-radiation.

13. A device according to claim 12 wherein said stem is formed from a fibre-reinforced plastics matrix.

14. A device according to claim 13, wherein said matrix is polyetherketone.

15. A device according to claim 13, wherein said matrix is reinforced by approximately 30% carbon fibre.

16. An ankle clamp device for external fixation of ankle bone fractures, said ankle clamp device being adapted for mounting to a distal end of a unilateral external fixator by means of at least one ball joint, the ankle clamp device comprising a stem with a bifurcate end formed with a pair of prongs, the stem having a stem axis and the prongs each having a free end, each of the free ends of the prongs having a bore, said bores defining a bore axis, said bore axis being transverse to the stem axis, the ankle clamp further comprising a tilting clamp including a first jaw portion and a second jaw portion, the ankle clamp device further comprising a transverse pivot having opposed ends, the bores through the prong ends being coaxial with each other and receiving respective opposed ends of said transverse pivot, said transverse pivot carrying said first jaw portion of the tilting clamp wherein the tilting clamp is journalled for pivotal movement between said prongs through said first jaw portion, the second jaw portion being coupled to the first jaw portion, the second jaw portion comprising a hole and the first jaw portion comprising a threaded socket, the ankle clamp device further comprising a screw disposed through the hole and engaged in the threaded socket, the pivotal movement of the tilting clamp being stopped by said screw passed through the hole in the second jaw portion and engaged in the threaded socket in the first jaw portion, said screw interfering with said pivot.

17. An ankle clamp device for external fixation of ankle bone fractures, said ankle clamp device being adapted for mounting to a distal end of a unilateral external fixator by means of at least one ball joint, the ankle clamp device comprising a stem with a bifurcate end formed with a pair of prongs, the stem having recesses formed laterally in each of the prongs, the ankle clamp further comprising a tilting clamp including a first jaw portion and a second jaw portion, the tilting clamp being journalled between said prongs through said first jaw portion.

18. A device according to claim 17, wherein said recesses are formed in a side of the prongs proximal a base of said bifrucate end.

19. A device according to claim 17 wherein said stem is formed from a fibre-reinforced plastics matrix transparent to X-radiation.

* * * * *